United States Patent [19]
Richards

[11] Patent Number: 5,696,245
[45] Date of Patent: Dec. 9, 1997

[54] FRUCTOFURANOSYL SUBSTITUTED POLYMERS AND METHODS FOR THEIR PRODUCTION

[75] Inventor: Geoffrey Richards, Missoula, Mont.

[73] Assignee: The University of Montana, Missoula, Mont.

[21] Appl. No.: 487,079

[22] Filed: Jun. 7, 1995

[51] Int. Cl.$^6$ .............................. C07H 15/24; C07G 3/00
[52] U.S. Cl. ............................................ 536/18.1; 536/4.1
[58] Field of Search .................................. 536/18.1, 4.1

[56] References Cited

U.S. PATENT DOCUMENTS

| | | | |
|---|---|---|---|
| 3,766,165 | 10/1973 | Rennhard | 260/209 R |
| 5,007,967 | 4/1991 | Ammeraal | 127/46.1 |
| 5,206,355 | 4/1993 | Richards et al. | 536/4.1 |

FOREIGN PATENT DOCUMENTS

WO 93/07159  4/1993  WIPO.

OTHER PUBLICATIONS

Formation of Trisaccharides (Kestoses) by Pyrolysis of Sucrose—Merilyn Manley–Harris and Geoffrey N. Richards—Carbohydrate Research, 219 (1991) 101–113.

Les β–cyclodextrines retardent La Germination de Embryons Somatiques de Carotte (Daucus Carota L.)—C.R. Acad. Sci. Paris, t.314, Serie III, pp. 171–177, 1992.

Inclusion Complexes of Poorly Water–Solube Drugs with Glucosyl–cyclodextrins—Chem. Pharm. Bull. 35 (8) 3413–3418 (1987).

Preparation, isolation, and characterization of novel heterogeneous branched cyclomaltooligosaccharides having β–D–galactosyl residue(s) on the side chain—Carbohydrate Research, 238 (1993) 75–91.

Isolation and characterization of Branched Cyclodextrins—Carbohydrate Research, 153 (1986) 55–67.

Some Properties and the Inclusion Behavior of Branched Cyclodextrins—Chem. Pharm. Bull 36 (6) 2176–2185 (1988).

Chemical & Pharmaceutical Bulletin—Inclusion Complexes of Lipids with Branched Cyclodextrins—vol. 37, No. 11, 3096–3099, Nov. 1989.

*Primary Examiner*—Johann Richter
*Assistant Examiner*—Ebenezer Sackey
*Attorney, Agent, or Firm*—Lowe, Price, LeBlanc & Becker

[57] ABSTRACT

A mixture of sucrose, an acid catalyst such as citric acid, and a natural or synthetic polymer such as a polysaccharide, starch or cyclodextrin is heated to generate a fructose oxocarbonium ion and transfer this ion from the sucrose to the polysaccharide, starch or cyclodextrin to form useful and novel fructofuranosyl substituted polysaccharides, starches and cyclodextrins.

21 Claims, 1 Drawing Sheet

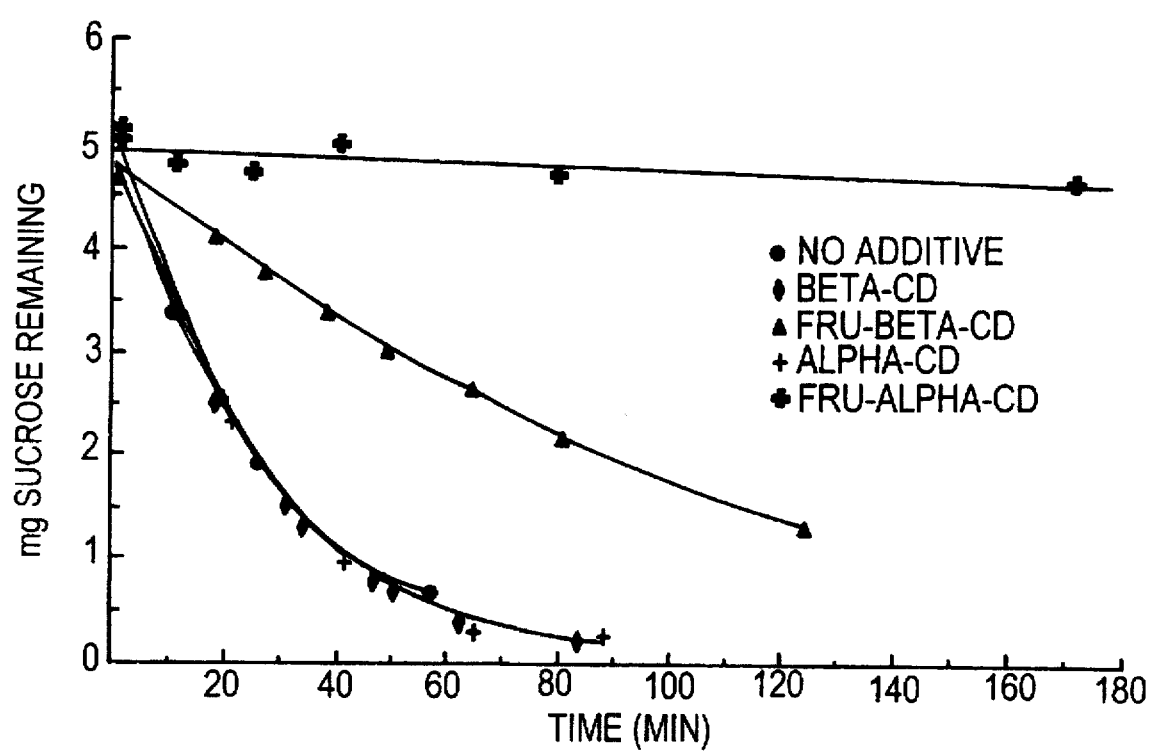

FRUCTOFURANOSYL SUBSTITUTED POLYMERS AND METHODS FOR THEIR PRODUCTION

FIELD OF THE INVENTION

This invention relates to substituted fructofuranosyl polysaccharides and similar polymers and their uses. More particularly, the present invention relates to a method for the production of fructofuranosyl substituted polysaccharides and other polymers, including starches and cyclodextrins, by reaction of a mixture of sucrose, a non-volatile acid, and a polysaccharide or similar polymer and transferring the fructose oxocarbonium ion from the sucrose as a fructofuranosyl group to the polysaccharide or similar polymer.

BACKGROUND OF THE INVENTION

The Applicant's prior studies concerning acid-catalyzed thermolysis of sucrose (Manley-Harris et al. Carbohydr. Res. 219 (1991) 101–113; U.S. Pat. No. 5,206,355) suggested that the pyrolysis of sucrose in the presence of an organic acid such as citric acid produced a resonance-stabilized fructofuranosyl oxocarbonium ion as a product of the scission of sucrose. This ion has been shown to react with alcohol groups by nucleophilic addition to produce fructosides from simple alcohols (Moody, et al., Carbohydr. Res. 97 (1981) 247–255), and oligosaccharides from unreacted sucrose (Manley-Harris, et al. *Carbohydr. Res.* 219 (1991) 101–113).

In the present invention, it has been discovered that this reaction can be used to thermally transfer fructosyl residues from sucrose to various polysaccharides and cyclodextrins and produce a series of new products.

SUMMARY OF THE INVENTION

It is accordingly one object of the invention to provide a method for the production of fructofuranosyl substituted natural and synthetic polymers such as polysaccharides, starches and cyclodextrins, by reaction of sucrose, an acid, and a polysaccharide, starch or cyclodextrin.

A still further object of the invention is to provide a novel group of fructofuranosyl substituted polysaccharides and cyclodextrins which are useful products.

Other objects and advantages of the present invention will become apparent as the description thereof proceeds.

In satisfaction of the foregoing objects and advantages, the present invention provides in one embodiment a novel class of fructofuranosyl substituted polysaccharides, starches and cyclodextrins.

The present invention also provides a method for the production of fructofuranosyl substituted natural and synthetic polymers such as polysaccharides, starches and cyclodextrins which comprises forming a mixture of sucrose, a non-volatile acid, and a polysaccharide, starch or cyclodextrin in which the fructofuranosyl group is to be substituted, and heating the mixture to cause transfer of a fructofuranosyl unit from the sucrose to the polysaccharide, starch or cyclodextrin.

The present invention also provides plant growth regulators which comprise as the effective ingredient, a fructofuranosyl substituted cyclodextrin.

BRIEF DESCRIPTION OF DRAWINGS

Reference is now made to the drawings accompanying the application wherein the sole Figure is a graph showing the action of invertase on sucrose in the presence of cyclodextrins and fructosyl cyclodextrins.

DESCRIPTION OF THE INVENTION

The present invention is concerned with a method for transfer of a resonance-stabilized fructofuranosyl oxocarbonium ion from sucrose to polysaccharides and other polymers such as cyclodextrins and starches, thereby producing fructofuranosyl units grafted to the polymer backbone. This invention is carried out either by thermolysis as a melt or in a solvent system as described below. According to this invention, it has been discovered that the reaction of a mixture of sucrose, a small amount of an acid, and a polymer as identified above, under conditions of heat, will cause transfer of one or more units of the fructose unit as a fructofuranosyl oxocarbonium ion to the polysaccharide or other polymer. The reaction may be carried out in a melt under pyrolysis conditions or may be carried out in a solvent system. In either system, there will be produced in the mixture a resonance-stabilized fructofuranosyl oxocarbonium ion of the following formula:

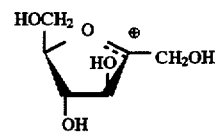

During the reaction, this fructofuranosyl oxocarbonium ion unit will transfer from the sucrose to the other polysaccharide or polymer present in the mixture, thereby producing one or more fructofuranosyl units grafted to the polymer backbone. As noted, the reaction may be carried out either in a melt system or in a polymer system. In the melt system, the reactants are mixed thoroughly and the mixture is then heated to a sufficient temperature to form a melt. In a preferred procedure, an aqueous solution of the reactants is formed and then freeze dried to remove the water and achieve good admixture in the form of a solid. The solid mixture is then heated to its molten form at the appropriate temperature, depending on the reactants. In general, the solid mixture will melt at a temperature in the range of 75° to 150° C. The melt is then thermalized for a period of 2 minutes to 2 hours, depending on the reactants, and then cooled. Thereafter, it is preferred to dissolve the reaction product in water, and add a lower alkyl alcohol (methanol, ethanol, propanol, etc.) at which point the fructose polymer precipitates since it is displaced from the water by the alcohol.

In the solvent system, sucrose, the polymer and the acid are dissolved in a suitable solvent, preferably dimethylsulfoxide (DMSO). In the solvent system, the polymer is dissolved in the solvent, the dry powder sucrose and acid catalyst are then added, and the solution is heated to a temperature of about 50° C. up to 150° C. at atmospheric pressure for 2 minutes to 2 hours to complete the reaction.

As indicated, the primary reactant is sucrose. In general, the sucrose should be combined with the acidic catalyst in the amount of about 0.2 wt. % to about 5.0 wt. %, based on the amount of sucrose in both systems. Preferably, about 1.0 wt. % of the acid catalyst should be combined with the sucrose for best results.

The acid catalyst is preferably a food grade acid, acid salt or acidic buffer. Suitable acids include organic acids which contain one or more characteristic carboxylic acid groups, and optionally a hydroxyl group, such as citric acid, tartaric acid, malic acid, benzoic acid, acetic acid or lactic acid. Inorganic acids such as phosphoric acid or sulfuric acid may also be used as well as acid salts and buffers thereof including sodium or potassium dihydrogen phosphate. These materials are referred to generally herein as "acid catalysts". The acid catalyst is preferably nonvolatile. Because of the minimum color obtained in the resulting products, and good reactivity, citric acid is an especially preferred reactant. Any acid catalyst which reacts in the process to produce the products indicated is considered to be within the scope of the invention.

The sucrose is combined with the polymer using about 5–20 parts of the polymer based on 100 parts of the sucrose. Preferably about 5 parts of sucrose per 1 part of polymer is employed in the reaction.

The polymer to be reacted with the sucrose which receives the fructofuranosyl unit, comprises any polysaccharide or similar polymer or any compound which can accept the fructofuranosyl unit. Starch compounds such as amylose and amylopectin, synthetic polymers such as polyvinyl alcohol, or other polymers which contain hydroxyl groups are suitable candidates for reaction.

Fructosyl (fructofuranosyl) substituted polysaccharides and cyclodextrins of the present invention provide a novel class of products unknown to the prior art. The fructosyl substituted polysaccharides include fructosyl amylose, fructosyl amylo pectins, and fructosyl soluble starches. All of these novel products have improved resistance to starch-degrading enzymes because of the presence of the fructosyl group. Further, the products are useful as low calorie starches since introduction of the fructosyl group converts the starches to low calorie starches. Further, substituted starches, such as fructosyl amylose, fructosyl amylo pectins and fructosyl soluble starches, have increased water solubility as compared to the starting product. Further, the fructosyl substituted amylose products have resistance to retrogradation from aqueous solutions.

In an especially preferred aspect of the invention, fructofuranosyl units are transferred from sucrose to a cyclodextrin to form a novel class of fructofuranosyl substituted products useful as plant growth regulators. Suitable cyclodextrins of this type include cyclohexaamylose, cycloheptaamylose and the like. Cyclodextrins in general are also known as cycloamyloses and cycloglucans. Cyclohexaamylose is sometimes known as alpha-cyclodextrin, cycloheptaamylose is known as beta-cylodextrin, and cyclooctaamylose is known as gamma-cyclodextrin.

According to this invention, novel branched cyclodextrins (CD's) are formed by the thermal transfer of one or more fructosyl residues from sucrose to 0–6 of one of the glucose residues of cyclohexaamylose, cycloheptaamylose or cyclooctaamylose. In each case, the fructosyl residue adds in the beta configuration. The resultant fructosyl cyclodextrins (Fru-CDS) show increased solubility in water and in the case of Fru-β-CD, increased ability to solubilize sparingly compounds by inclusion, as compared to the parent cyclodextrins. The Fru-CD's have similar abilities to form complexes as their respective parent CD's and also act as inhibitors of invertase. The novel branched Fru-CD's of this invention thus have usefulness in the food and drug industries as solvents since they have the ability to solubilize sparingly soluble compounds such as drugs.

The invention has been described herein with reference to certain preferred embodiments. However, its obvious variations thereon will become apparent to those skilled in the art, the invention is not to be considered as limited thereto.

EXAMPLE 1

Before any transfructosylation experiments were attempted, it had to be shown that no degradation of amylose occurred under conditions known to induce the thermolysis of sucrose. This was done by measuring the change in the relative viscosity of solutions containing amylose and 10 mM $H_2SO_4$ in dimethyl sulfoxide before and after heating for 2 hours at 50° C. The relative viscosity before heating was 2.74 and after heating was 2.71. It was concluded that very little degradation of the amylose had occurred.

Starting with conditions similar to those used in the viscosity determination experiments, the optimization of transfructosylation was performed by varying acidity, temperature, time and reactant ratios and determining the fructose to glucose ratios in the resulting fructosyl amylose products by combined cysteine-carbazole and sulfuric acid colorimetric analyses. Results are shown in Table 1. Conditions of 50° C./2 hr/sucrose:amylose (5:1 w/w)/10 mM $H_2SO_4$ were chosen for convenience and efficiency and on a large scale, gave a fructosyl amylose product containing 4.6% fructose (i.e., ca 1 fructose residue:22 glucose residues).

The fructosyl amylose polymer was analyzed using conventional methylation analysis and compared with amylose. In order to detect the presence of fructose residues, which are subject to acid degradation in the hydrolysis phase of methylation analysis, a double procedure using mild and strong hydrolysis was performed on duplicate samples of the fructosyl amylose. Gas chromatography/mass spectrometry (GC/MS) from the mild hydrolysis procedure showed only 2,5-di-O-acetyl-1,3,4,6-tetra-O-methylhexitol(s) resulting from fructofuranosyl grafted units. The strong hydrolysis procedure, followed by GC/MS and gas chromatography/flame ionization detection (GC/FID) (corrected for carbon response) showed products from glucopyranose units which were 1,4 linked-(1.00), 1,4,6-linked (0.048) and 1-linked (0.021). The excess of the 1,4,6-linked glucose units over nonreducing end groups was evidently due to fructose units grafted only at $O_6$ of in-chain glucose units of the amylose. The relative amount of such units from the methylation analysis corresponds to 4.5% of the product polysaccharide and agrees well with the fructose content of 4.6% from colorimetric determination of the fructose:glucose ratio. The grafted fructose units are evidently in the furanose form as shown by the identity of the tetramethylhexitol(s). That grafting occurs only at $O_6$ of the amylose was expected from earlier studies with primary and secondary alcohols. There is no further addition of fructose cation to fructose units already grafted to the amylose (i.e. all of the fructose is present as single unit side chains). By analogy with previous results, it was assumed that the fructofuranoside units are both α- and β-linked and that the general structure is as shown in (2).

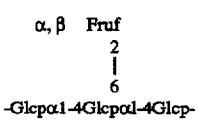

Examples of the extent of fructosyl transfer under varied conditions are shown in Table I:

TABLE 1

Fructosylation of Amylose

| CONDITIONS | | | | | |
|---|---|---|---|---|---|
| TEMP °C. | TIME Hrs. | SUCROSE: AMYLOSE | $H_2SO_4$ mM | Yields % based on amylose | % FRUCTOSE |
| 70 | 1 | 1:1 | 10 | 98 | 1.6 |
| 70 | 1 | 2:1 | 10 | 98 | 2.9 |
| 70 | 1 | 5:1 | 10 | 96 | 4.2 |
| 85 | 0.5 | 5:1 | 10 | 94 | 3.2 |
| 55 | 3 | 5:1 | 10 | 103 | 6.4 |
| 42 | 9 | 5:1 | 10 | 106 | 7.6 |
| 25 | 65.5 | 5:1 | 10 | 102 | 7.9 |
| 42 | 4.5 | 5:1 | 20 | 106 | 6.7 |

The fructose units appended to the amylose chain at average intervals of ca. 20 glucose units were expected to interfere with formation of extended sequences of the stable amylose helix which contains about six glucose units per turn. This question was addressed by study of the iodine complex. The complex of $I_2$/KI with amylose had $\lambda_{max}$634 nm, whereas the fructosyl amylose had $\lambda_{max}$584 nm, showing a complex which is less blue, indicates a partial transition towards a red iodine complex similar to that shown by amylopectin and which is generally associated with disruption or inhibition of the formation of extended helixes by branches in the amylopectin chain.

The retrogradation of amylose from aqueous solution is generally believed to be due to alignment and hydrogen-bonding of molecules to form "bundles" and eventually insoluble particles. The presence of fructose units along the amylose chain was expected to inhibit such alignment and bonding along the chains and hence to reduce retrogradation. Accordingly, it was found that under conditions where a neutral amylose solution showed 75% precipitation due to retrogradation in 24 hrs, the corresponding fructosyl amylose showed no precipitation.

The hydrolysis of starches to glucose by amyloglucosidase is generally complete because this enzyme attacks both α-1,4 and α-1,6 glucosyl linkages. It was anticipated however that the presence of the fructofuranosyl group at intervals along the amylose backbone would stop the progressive action of this exo-enzyme. Accordingly, it was found that under conditions where amylose was 86% converted to apparent glucose (measured by reducing power), the fructosyl amylose was only 29% converted. At this stage the hydrolysis of the fructosyl amylose was still proceeding at a significant rate however, and it is possible that the α-glucosidase can slowly attack the fructofuranosyl linkages. The digests at 29% conversion showed glucose and a trace of fructose, but no oligosaccharides.

With α-amylase, starches are attacked in endo-fashion, although there is some resistance to hydrolysis at or near branch points in amylopectin. The action of α-amylase on fructosyl amylose (as indicated by increase in reducing power) was only slightly less extensive than with amylose, e.g., an apparent conversion to glucose (by reducing power) of 52% with amylose and 43% with the fructosyl amylose in 300 minutes. Liquid chromatography (LC) of the latter products at this stage, suggested the presence of oligosaccharides containing about 5–7 hexose units, but with slightly different retention times from the corresponding maltodextrins. Presumably these contain a fructose unit, but they were not further investigated. It was concluded that the α-amylase probably does not readily attack the fructofuranosyl linkages in fructosyl amylose.

EXAMPLE 2

Amylopectin was also treated with sucrose and $H_2SO_4$ in the same way as amylose above. The resulting fructosyl amylopectin (obtained in 104% yield based on amylopectin) had 5.8% fructose by colorimetric analysis. Methylation analysis was carried out using both mild and strong hydrolysis and compared with the original amylopectin. The mild hydrolysis showed that the fructose was present only as a non-reducing fructofuranosyl end group. The strong hydrolysis showed by GC/FID quantitation (corrected for e.c.r.) that in the original amylopectin there were 14 unbranched in-chain glucose units for each branched glucose unit. In the fructosyl amylopectin, the same analysis showed eight unbranched in-chain glucose units for each branched glucose unit. It was concluded that the fructosyl amylopectin contains about as many fructose-branched in-chain glucose units as "normal" branched units. This value requires a fructose content of 5.3% if all of the fructose branches are single fructose units and it was concluded that this is the case, since the colorimetric analysis indicates 5.8% fructose content and since no non-end group fructose units were detected. The fructosyl amylopectin therefore carries single fructofuranosyl units at $O_6$ about equal in number to the original 1–6 branch points of the amylopectin.

The action of the exo β-amylase on the fructosyl amylopectin was compared with the original amylopectin. The conversion limit was reached in the same time in both instances, with the original amylopectin showing 66.3% conversion to apparent maltose (by colorimetry) and the fructosyl amylopectin showing 31.7% conversion. These values are compatible with the above concept of the fructosyl amylopectin structure.

EXAMPLE 3

By freeze-drying an aqueous solution of beta-cyclodextrin (β-CD) with a five-fold excess of sucrose and 1.0 wt. % citric acid catalyst (based on sucrose), a solid was obtained which melted to a colorless liquid at 115° C. The mixture prepared in this manner was thermolyzed at 120° C. for 30 minutes and the resultant melt was examined by liquid chromatography (LC) using two different systems. In an $NH_2$-bonded silica column with acetonitrile-water eluant, a product, 2, was observed running more slowly than the parent CD indicating increased molecular size. With a $C_{18}$-bonded silica column and methanol-water eluant 2 ran more rapidly than the parent CD indicating greater solubility in water and this system was employed for preparative LC. The yield of 2 based on relative LC peak areas was 21% of the starting CD. Attempts to precipitate 2 from an aqueous solution of the thermolysis product mix using ethanol-acetone or cyclohexane resulted in augmentation of the parent CD in the precipitate presumably due to the greater solubility of the complexes of 2.

In addition to 2, a lesser amount of another faster-running product, 3, was isolated by preparative LC. A further faster-running peak proved to be a highly-colored polymeric material and was probably an unsaturated fructose degradation product.

Colorimetric assay of 2 and 3 gave glucose:fructose ratios of 6:1 and 2.3:1 respectively. Methylation analysis of 2 using mild hydrolysis (Manley-Harris et al. *Carbohydr. Res.* 240 (1993) 183–196) revealed the presence of a fructofuranosyl residue linked at only C-2. Strong hydrolysis of per-O-methylated 2 demonstrated the presence of glucopyranosyl residues linked 2,4 and 2,4,6 in the ratio 6:1. A similar treatment of 3 showed the presence of a variety of fructosyl residues and 1,4- and 1,4,6-linked glucopyranosyl residues in the ratio 4.5:1. It was decided that 3 represented a mixed product so it was not pursued further. It is however probable that 3 contained β-CD units carrying more than one fructose at 0–6 of glucose residues or possibly fructosyl chains of two or more units.

Immediately after LC separation and drying, 2 was pale yellow in color but after treatment with carbon in aqueous solution it could be dried to a colorless glass. It is probable that unsaturated degradation products complex with 2 and pass with it through the LC column.

FAB-MS of 2 gave a peak at 1298[M+H]$^+$ and a series of peaks corresponding to [M-(162)$_n$]$^+$ confirming the presence of a single fructosyl residue on the CD. The $^{13}$CNMR spectrum showed the presence of a β-linked fructofuranosyl residue. No trace of the α-anomer could be detected.

On the basis of this evidence, 2 was assigned as 6-O-(β-D-fructofuranosyl) cycloheptaamylose. A similar treatment of a α-CD yielded 6-O-(β-D-fructofuranosyl) cyclohexaamylose, 4 (34% yield).

The solubilities of 2 and 4 were determined as were their respective abilities to solubilize a slightly soluble drug. The results are summarized in Tables 2 and 3.

TABLE 2

Solubility in water of CD's and Fru-CD's

| Compound | Solubility (mg/mL)* |
| --- | --- |
| cyclohexaamylose (α-CD) | 126 |
| 6-O-(β-D-fructofuranosyl) cyclohexaamylose (Fru-α-CD) | 1054 |
| cycloheptaamylose (β-CD) | 20 |
| 6-O-(β-D-fructofuranosyl cycloheptaamylose (Fru-β-CD) | 1136 |

*determined at 21° C. ± 1° C.

TABLE 3

Solubility of Estriol in Water in Presence of CD's and Fru-CD's at 20° C.

| Solubility in water (μg/mL) | Solubility in 1.5 × 10$^{-2}$ M CD solution (μg/mL | | | |
| --- | --- | --- | --- | --- |
| | α-CD | Fru-α-CD | β-CD | Fru-β-CD |
| 23 | 33 | 29 | 747 | 1909 |

2 and 4 were unaffected by invertase under conditions that brought about the complete hydrolysis of sucrose in 30 minutes. In a 1:1 mole ratio with sucrose 2 and, to a much greater extent, 4 demonstrated inhibition of invertase, (see attached Figure). No inhibition was manifested by the parent CD's. A more detailed kinetic study is required to determine the nature of the inhibition, but in the meantime it is noted that these results indicate that the Fru-α-CD appears to be a non-reversible inhibitor of the hydrolysis of sucrose by invertase. Furthermore, provided that the Fru-α-CD is capable of transport to regions of plants or of plant cells, where invertase action occurs, then it is a potent plant growth regulator.

EXAMPLE 4

Preparation of Fructosyl-Amylopectin (FruAP)

Amylopectin (10.25 g, moisture content 10.3%, Sigma Chemical Co. from corn), sucrose (50.0 g) and citric acid (0.60 g) were dissolved in water (450 mL) and freeze-dried to yield a brittle, white, solid foam. A sample of this product began to melt at 89° C. and became a clear, colorless liquid by 104° C. A further sample (1.01 g) was crushed to a thin layer in a 50 mL Ehrlenmeyer flask and heated in an oven at 140°±1° C. for 30 minutes. The resultant pale yellow melt was cooled, dissolved in water, neutralized with NH$_4$OH and the product precipitated with ethyl alcohol (100 mL). The precipitate was redissolved in water and reprecipitated, then washed with ethyl alcohol EtOH and dried to a white powder (0.150 g) described herein as FruAP.

Colorimetric assay of the FruAP product indicated a fructose content of 12%. Mild hydrolysis followed by reduction and per-O-trimethylsilylation using an internal standard indicated an 8% fructose content. For steric reasons 1 would be expected to add predominantly to primary hydroxyls that is to 0–6 of glucose. Addition of fructose would therefore be expected to result in an increased number of apparent 1,4,6-branch points. Methylation analysis indeed revealed an increase in the number of these branch points from 7%, that is ~14 unbranched in-chain glucose residues for every branched residue in amylopectin to 17% in FruAP, that is ~5 unbranched in-chain glucose residues for every branched glucose residue; no evidence was found of other than 1,4,6-branch points. However, methylation analysis gives no indication of the presence of fructose attached to other fructose units since the strong hydrolysis conditions, which are required to cleave the amylopectin chain, completely destroy the fructose residues. Mild hydrolysis of per-O-methylated FruAP revealed only 2-linked fructofuranose units indicating that fructose residues which have been further substituted, if they do exist, are an insignificant proportion of the total fructose.

EXAMPLE 5

Preparation of Fructosyl Soluble Starch

Soluble Starch (10.0 g moisture content 11.5% Sigma Chemical Co. A.C.S. reagent), sucrose (50.0 g) and citric acid (0.60 g) were dissolved in water (250 mL) and freeze-dried. A sample (2.00 g) of the product was heated as above at 120° C. for 100 minutes, precipitated twice from water with ethyl alcohol and dried to a white powder (0.32 g) described herein as FruSS.

Colorimetric assay of FruSS indicated 12% fructose. Mild hydrolysis followed by reduction and per-O-trimethylsilylation revealed, by GC-FID, 14% fructose. Methylation analysis showed an increase in branched residues from 4% in untreated soluble starch to 14% in FruSS. The latter value is not a measure of the total fructose present since mild hydrolysis of the per-O-methylated FruSS showed that ~20% of the fructose residues were 1,2- or 2,6-linked, that is to say chains of two or more fructose units were attached at some branch points. The $^1$H NMR spectrum of FruSS showed signals corresponding to H-3 and H-4 of fructose and the $^{13}$C NMR spectrum contained small signals at 108.9 and 104.8 ppm indicating the presence of both α- and β-linked fructofuranosyl residues.

Enzyme studies—The β-amylase limit for amylopectin was 55% conversion to apparent maltose whereas the limit for FruAP was 9%. The exo-acting β-amylase is therefore unable to degrade the polymer past a branch-point whether it be due to a glucosyl or fructosyl residue attached at C-6. The β-amylase limit for soluble starch was 64% conversion whereas that for the FruSS was 0%. This rather startling observation was confirmed by repeating the experiment twice, the second time being with a ten-fold increase in the concentration of the enzyme. The FruSS bears a fructosyl residue on every eighth residue on average and it would appear from these results that the fructosyl branches are partly concentrated near the non-reducing ends of the soluble starch molecules.

The present invention has been described herein with reference to certain preferred embodiments. However, as obvious variations thereon will become apparent to those skilled in the art, the invention is not to be considered as limited thereto.

I claim:

1. A method for the production of fructofuranosyl substituted natural or synthetic polymers which comprises combining sucrose, an acid catalyst, and a natural or synthetic polymer, and heating the mixture at a sufficient temperature and for a sufficient time to transfer at least one fructofuranosyl unit from the sucrose to the natural or synthetic polymer.

2. A method according to claim 1, wherein the natural or synthetic polymer is a polysaccharide or a cyclodextrin.

3. A method according to claim 2, wherein the acid catalyst is a non-volatile organic acid or inorganic acid and is present in an amount of about 0.2 wt. % to about 5.0 wt. %, based on the weight of sucrose.

4. A method according to claim 2, wherein the acid catalyst is selected from the group consisting of organic carboxylic acids and inorganic acids.

5. A method according to claim 3, wherein the acid catalyst is selected from the group consisting of citric acid, tartaric acid, malic acid, benzoic acid, lactic acid, phosphoric acid, and sulfuric acid, or salt or buffer thereof.

6. A method according to claim 1, wherein the acid catalyst is citric acid.

7. A method according to claim 2, wherein the polymer to be reacted with sucrose and receive the fructofuranosyl unit is a polysaccharide.

8. A method according to claim 2, wherein the polymer to be reacted with the sucrose and receive the fructofuranosyl unit is a starch.

9. A method according to claim 8, wherein the starch is a soluble starch, an amylose or an amylopectin.

10. A method according to claim 2, wherein the polymer to be reacted with the sucrose and receive the fructofuranosyl unit is a cyclodextrin.

11. A method according to claim 10, wherein the cyclodextrin is selected from the group consisting of cycloamyloses and cycloglucans.

12. A method according to claim 1, wherein the sucrose is combined with the polymer in amounts of about 5–20 parts of polymer per 100 parts of sucrose.

13. A method according to claim 1, which comprises reaction of sucrose with about 5–20 parts of a polysaccharide, starch or cyclodextrin per 100 parts of sucrose in the presence of about 0.2–5.0 wt. % of an acid catalyst, based on the weight of the sucrose, to produce a fructofuranosyl substituted polysaccharide, starch or cyclodextrin.

14. A method according to claim 1, wherein the reaction is carried out in molten form by combining the sucrose, acid catalyst and polymer to form an intimate mixture, heating to form a melt and continuing heating for a sufficient time for thermolysis occur and transfer at least one fructofuranosyl unit from the sucrose to the polymer.

15. A method according to claim 14, wherein heating is carried out at a temperature in the range of 75°–200° C. for about 2 minutes to 2 hours.

16. A method according to claim 15, wherein after completion of thermolysis, the mixture is cooled, dissolved in water, a lower alkyl alcohol is added thereto and the fructofuranosyl substituted polymer recovered therefrom.

17. A method according to claim 1, wherein the reaction is carried out in a solvent system by dissolving the sucrose, polymer and acid catalyst in a solvent, heating at a temperature of about 50° to about 150° C. for a period of 2 minutes to 2 hours, and recovering the product.

18. A method according to claim 14, wherein the catalyst is an organic or inorganic acid present in an amount of about 0.2–5.0 wt. %, based on the amount of sucrose.

19. A method according to claim 17, wherein the solvent is dimethyl sulfoxide.

20. A fructofuranosyl substituted polymer prepared by the method of claim 1.

21. A substituted polymer according to claim 20, wherein the polymer is a polysaccharide, starch or cyclodextrin.

* * * * *